United States Patent [19]

Lee et al.

[11] 4,371,712

[45] Feb. 1, 1983

[54] ALKYLSALICYLALDEHYDE PREPARATION

[75] Inventors: Richard J. Lee, Downers Grove; Leonard J. Baranowski, Winfield, both of Ill.

[73] Assignee: Standard Oil Company (Indiana), Chicago, Ill.

[21] Appl. No.: 313,798

[22] Filed: Oct. 22, 1981

[51] Int. Cl.³ ............................................. C07C 45/00
[52] U.S. Cl. .................................... 568/430; 568/442
[58] Field of Search .................... 568/442, 430, 426

[56] References Cited

U.S. PATENT DOCUMENTS 3,098,875  7/1963  Schmerling .................... 568/428
4,151,201  4/1979  Casnati et al. ................. 568/442 X

*Primary Examiner*—Bernard Helfin
*Attorney, Agent, or Firm*—Richard A. Kretchmer; William T. McClain; William H. Magidson

[57] ABSTRACT

An alkyl-substituted salicylaldehyde whose alkyl-substituent contains at least 6 and up to 2000 or more carbon atoms are novel composition of matter. Said novel alkylsalicylaldehyde can be prepared by the novel reaction of an alkylphenol containing at least six carbon atoms and up to 2000 or more carbon atoms in the phenol's alkyl-substituent, a dialkyloxy methane and a peroxide in the presence of a free radical forming catalyst.

13 Claims, No Drawings

ALKYLSALICYLALDEHYDE PREPARATION

This invention relates to novel alkyl-substituted salicylaldehyde and its novel preparation from an alkyl-substituted phenol, a dialkoxy alkane and a peroxide. More particularly the invention pertains to novel oil soluble alkyl-substituted salicylaldehyde (i.e., alkyl of at least six carbon atoms) and its novel preparation from a $C_6$-alkyl and higher alkylphenol, a dialkoxy methane in the presence of a peroxide and a manganese catalyst.

BACKGROUND OF THE INVENTION

In the past to make use of the anti-oxidant anti-corrosion properties in only hydrocarbons imparted by Ca salicylaldimine

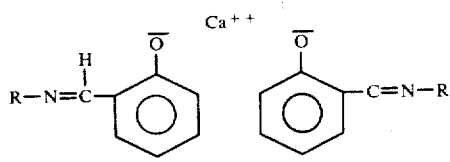

wherein R is alkyl, an aminoethyl ($H_2N_2$-$CH_2CH_2$-), hydroxyethyl (HO-$CH_2CH_2$-) or thiolethylene (HS-$CH_2,CH_2$-), it has been necessary to prepare a derivative of the salicylaldimine which would make it soluble in oily hydrocarbons such as distillate fuels (gasoline, diesel fuel, heating oil, etc.) and lubricant oils. For example, according to U.S. Pat. No. 3,296,130 a salicylaldimine where R is $CH_2CH_2CH_2$-$NH_2$ is reacted with an oil-soluble aklenyl-substituted succinic acid (alkenyl-substituent was tetrapropenyl).

The same oxidation and/or corrosion inhibition of an salicylaldimine could be made available providing solubility in oily hydrocarbons could be imparted to salicylaldehyde from which the imines were derived by the known Schiff Reaction between an aldehyde and an amine. To impart such solubility in an oily hydrocarbon it would be necessary to substitute one of the ring carbons an alkyl-substituent having at least six carbon atoms. However, alkylation of the salicyl moiety by conventional means is sufficiently difficult to make it commercially unattractive. It is known that an oil soluble salicylic acid can be prepared through a modified Kolbe reaction wherein a solution of a sodium phenate salt of a $C_6$ or higher alkyl-substituted phenol is reacted with carbon dioxide.

However, our search of the prior art did not bring to light any alkylation of salicylaldehyde or reaction of an alkyl-substituted phenol for the preparation of a commercially feasible route to an alkyl-substituted salicylaldehyde which would be soluble in an oily hydrocarbon such as the distillate fuels and lubricant oils.

We have found a rather simple and commercially feasible route for the preparation of an alkyl-substituted salicylaldehyde which will be soluble in said oily hydrocarbons.

STATEMENT OF THE INVENTION

An alkyl-substituted salicylaldehyde having an alkyl-substituent containing six or more carbon atoms can be made from the corresponding phenol by reacting it with a dialkoxy methane such as dimethoxy methane, diethoxy methane, and the like in the presence of a peroxide (e.g., tertiary-butyl peroxide, benzoyl peroxide, peracetic acid, and the like) and in the presence of free radical promoting catalyst, such as a manganese catalyst in the ionic form. The foregoing reaction results in the dialkoxy-methylation of the alkylphenol on an unsubstituted ring carbon atom in the position ortho to the carbon having the hydroxyl-substituent. The dialkoxymethyl alkylphenol in an acidic environment and in the presence of water is converted to the $C_6$ and higher alkyl-substituted salicylaldehyde and the alkanol corresponding to the alkoxy group of the dialkoxy methane as a co-product.

The dialkoxy methane reactant of choice is dimethoxy methane or its equivalent sym-trioxane because such preferred reactant results in most readily removed methanol or formaldehyde as co-product. Excess dialkoxy methane is also readily removed. It is therefore, desirable to use the dialkoxy methane reactant in excess of equimolecular proportions. Preferably from 5 to 20 gram moles of dimethoxy methane per gram mole of alkyphenol.

A moderate reaction temperature of from $-5°$ C. up to $45°$ C. is employed at atmospheric (0 gauge) pressure.

A reaction diluent inert of the free radical dialkoxy reaction is advantageously used to make the reaction mixture less viscous and more flowable at reaction temperature. Alkanes of boiling temperatures in the range of from pentane ($36°$ C.) up to octane ($125°$ C.) cycloheptane and cyclohexane, acetic and propionic acids are suitable reaction diluents.

The ionic manganese catalyst can be provided by manganous or manganic salts soluble in the reaction diluent or alkylphenol reactant. Manganous acetate, naphthenate, or acetyl acetonate as well as manganic acetyl acetonate are suitable sources of ionic catalyst in the methoxy-methylation of the alkyl phenol.

As indicated above the alkylphenol reactant should have at least one available hydrogen atom on a ring carbon ortho to the ring carbon which the hydroxyl group is attached. Thus a p-alkylphenol readily satisfies the requirement for the presence of at least one unsubstituted ring ortho-carbon atom. However other mono-alkyl-substituted phenols also can be used as reactants. The alkylphenol reactant can be hexylphenol, heptylphenol, octylphenol, nonylphenol, decylphenol, hindecylphenol, dodecylphenol, tridecylphenol, tetradecylphenol, pentadecylphenol, hexadecylphenol, heptadecylphenol, octadecylphenol, nonadecylphenol, eicosylphenol, henicosylphenol, docosylphenol, tricosylphenol, tetracosylphenol pentacosylphenol, hexacosylphenol, heptacosylphenol, octacosylphenol, nonacosyophenol, the triacontylphenols, the tetracontylphenols, the pentacontylphenols, the hexacontylphenols, the heptacontylphenols, the octacontylphenols and the nonacontylphenols through nonanonacontylphenol which in general are n-alkylphenols containing 6 to 99 carbon atoms. However, the alkyl-substituents on the para ring carbon atom of phenol can also be branched as are those derived from olefins obtained as a fraction or reaction product of petroleum refining including distillation, cracking and reforming processes. The p-alkyl-substituent of the alkylphenol reactant can also be synthesized as, for example, by the Friedel-Craft catalyzed (especially aluminum chloride catalyzed) polymerization of propylene and butenes especially mixtures of isomeric butenes whose polymers predominate in isobutyl units. Such polymers are mono-olefinic. The alkylation of phenol with such propylene and butene polymers containing from 6 up to 2000 carbon atoms in the presence of boron trifluoride as catalyst provides predominantly a p-alkylphenol as the alkylation reaction product. Polyisobutylene, having more than 2000 carbon atoms and isobutylene copolymers such as the butyl rubbers can be used as the alkylating agent to provide alkylphenols whose alkyl-substituents contain more than 7000 carbon atoms.

While coming within the concept of the present invention, the alkylphenols whose alkyl groups have more than about 200 carbon atoms are highly viscous liquids or are solids whose alkyl phenols give rise to an alkylsalicylimines which adversely thicken the oily hydrocarbon to which oxidation and/or corrosion inhibition is to be imparted. Therefore, if only as a practical matter, the alkylphenol reactants preferred for the present invention are those whose alkyl-substituent contains from 6 to 200 carbon atoms.

The foregoing alkylphenols and their preparation are known, for example, from U.S. Pat. Nos. 3,235,484, now Reissue Patent Re. 26,330; 3,360,464; and British Patent Specification No. 1,159,368.

The present invention will be illustrated by the following examples from which those skilled in the art can readily perceive other alkylsalicylaldehydes and their preparation coming within the scope of the appended claims.

EXAMPLE 1

To 250 cc (2.9 moles) of dimethoxy methane there is added 200 grams (0.25 mole) of alkylphenol whose alkyl-substituent contains 66 carbon atoms. The mixture is stirred in a flask from which oxygen (air) can be excluded. The stirred mixture and the vapor space thereabove is purged of oxygen with nitrogen gas. Thereafter, while under a nitrogen blanket, 12 cc of tertiary butyl peroxide (and/or 1.0 gram of benzoyl peroxide) are added slowly so the resulting mixture remains at ambient (20° C.) temperature. Said resulting mixture is stirred and heated slowly to 30° C. and then finally to 44° C. the reaction mixture boils and the resulting vapors are cooled to provide liquid reflux. Such refluxing, at 44° C. is maintained for two hours. Thereafter the reaction mixture is further heated to a final temperature of 150° C. which bubbling nitrogen gas into the reaction mixture to drive off co- and by-products. By analysis it is found that the C-alkyl-substituted salicylaldehyde produced amounts to a yield which is 68% of theoretical yield.

EXAMPLE 2

To 38 grams (0.5 mole) of dimethoxy methane in a flask fitted with a stirrer there is added 26 grams (0.1 mole) of dodecylphenol and 50 milligrams of manganic acetylacetonate dissolved in 50 ml of glacial acetic acid. The mixture is stirred and cooled to −4° C. and then 40 grams of 40% peracetic acid are added dropwise over a 45 minute period while maintaining the resulting mixture at −4° C. for 60 minutes thereafter the mixture is permitted to warm to 20° C. When the mixture remained at 20° C. without externally applied cooling, the mixture is heated to remove methanol and acetic acid. The yield of dodecylsalicylaldehyde is found to be 98% of the theoretical yield.

EXAMPLE 3

The preparation method of Example 2 is repeated except that for the dodecylphenol there is substituted 0.1 gram mole of alkylphenol whose alkyl-substituent contains 158 carbon atoms and was derived from a butene polymer. The yield of the $C_{158}$ alkyl-substituted salicylaldehyde is found to be 61% of the theoretical yield.

EXAMPLE 4

The preparative method of Example 2 is repeated except for the dodecylphenol there is substituted 0.1 gram mole of alkylphenol whose alkyl group contains carbon atoms derived from a propene polymer. The yield of the $C_{66}$ alkyl-substituted salicylaldehyde is found to be 64% of the theoretical yield.

The invention claimed is:

1. A method of preparing an alkylsalicylaldehyde whose alkyl-substituent contains at least 6 carbon atoms which method comprises reacting an alkylphenol whose alkyl-substituent contains at least 6 carbon atoms with a dialkoxymethane in the presence of a peroxide and in the presence of a free radical forming ionic manganese catalyst at a temperature of about the peroxides decomposition.

2. The method of claim 1 wherein the dialkoxymethane is dimethoxymethane, the peroxide is peracetic acid, benzoyl peroxide or tertiary-butyl peroxide and the manganese catalyst is manganous acetate, manganous naphthenate or manganic acetyl acetonate.

3. The method of claim 1 wherein the alkylphenol has an alkyl-substituent which is straight or branched and contains 6 to 200 carbon atoms.

4. A method for preparing an alkyl-substituted salicylaldehyde which comprises reacting an alkylphenol with a dialkoxymethane in the presence of a peroxide and a free radical promoting catalyst, wherein the alkyl substituent of said alkylphenol contains at least six carbon atoms.

5. The method as set forth in claim 4 wherein said catalyst comprises manganese.

6. The method as set forth in claim 5 wherein said catalyst is selected from the group consisting of manganous acetate, manganous naphthenate, manganous acetyl acetonate and manganic acetyl acetonate.

7. The method as set forth in claim 4 wherein said peroxide is selected from the group consisting of tertiary-butyl peroxide, benzoyl peroxide and peracetic acid.

8. The method as set forth in claim 4 wherein the alkyl substituent of said alkylphenol contains from 6 to 2000 carbon atoms.

9. The method as set forth in claim 8 wherein the alkyl substituent of said alkylphenol contains from 6 to 200 carbon atoms.

10. The method as set forth in claim 8 wherein the alkyl substituent of said alkylphenol is n-alkyl.

11. The method as set forth in claim 8 wherein the alkyl substituent of said alkylphenol comprises repeating propyl units.

12. The method as set forth in claim 8 wherein the alkyl substituent of said alkylphenol comprises repeating isobutyl units.

13. The method as set forth in claims 1 or 4 wherein the reaction product of said alkylphenol and dialkoxymethane is contacted with water in an acidic environment.

* * * * *